US00PP29299P2

(12) United States Plant Patent
Scheys

(10) Patent No.: US PP29,299 P2
(45) Date of Patent: May 15, 2018

(54) ***HEUCHERA* PLANT NAMED 'FLORES SEA'**

(50) Latin Name: ***Heuchera* hybrid**
Varietal Denomination: Flores Sea

(71) Applicant: Diederik Alexander Maria Scheys, Réty (FR)

(72) Inventor: Diederik Alexander Maria Scheys, Réty (FR)

( * ) Notice: Subject to any disclaimer, the term of this patent is extended or adjusted under 35 U.S.C. 154(b) by 0 days. days.

(21) Appl. No.: 15/330,005

(22) Filed: Jul. 25, 2016

(51) Int. Cl.
*A01H 5/12* (2018.01)

(52) U.S. Cl.
USPC ..... Plt./440

(58) Field of Classification Search
USPC ..... Plt./440
CPC ..... A01H 5/02; A01H 5/025; A01H 5/00; A01H 5/12
See application file for complete search history.

(56) References Cited

U.S. PATENT DOCUMENTS

PP12,066 P2 * 8/2001 Oliver ..... Plt./440
PP18,324 P2 * 12/2007 Egger ..... Plt./440

OTHER PUBLICATIONS

New Plants and Flowers Three *Heuchera* varieties with 'unique' foliage, Mar. 28, 2015, retrieved on Aug. 14, 2017, retrieved from the Internet at http://www.newplantsandflowers.com/three-heuchera-varieties-with-unique-foliage/ 2 pp.*

* cited by examiner

*Primary Examiner* — June Hwu
(74) *Attorney, Agent, or Firm* — Penny J. Aguirre

(57) ABSTRACT

A new cultivar of *Heuchera* named 'Flores Sea', characterized by its remontant blooming habit, its dense flower panicles, its very large flowers that are pink in color, and its leaf coloration that is silver with dark olive veins.

2 Drawing Sheets

Botanical classification: *Heuchera* hybrid.
Cultivar designation: 'Flores Sea'.

BACKGROUND OF THE INVENTION

The present invention relates to a new and distinct cultivar of *Heuchera*, botanically of hybrid origin and known as a *Heuchera* 'Flores Sea' and is hereinafter referred to by its cultivar name 'Flores Sea'.

The new cultivar was derived from a controlled breeding program conducted by the Inventor in Pellenberg, Belgium. The overall purpose of the breeding program is to develop a new cultivar of *Heuchera* plant with attractive foliage in combination with attractive flowers that are remontant.

'Flores Sea' originated from the open pollination of unnamed and unpatented seedling of *Heuchera sanguinea* from the Inventor's breeding program in June of 2008. The male parentage is therefore unknown but presumed to be of hybrid origin based on the characteristics of the new cultivar. 'Flores Sea' was selected as a single unique plant in May of 2009 from amongst the resulting seedlings.

Asexual propagation of the new cultivar was first accomplished by tissue culture using meristem tissue under the direction of the Inventor in Beervelde, Belgium in May of 2009. Asexual propagation of the new cultivar by tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Flores Sea' as a new and unique cultivar of *Heuchera*.

1. 'Flores Sea' exhibits a remontant blooming habit.
2. 'Flores Sea' exhibits dense flower panicles.
3. 'Flores Sea' exhibits very large flowers that are pink in color.
4. 'Flores Sea' exhibits leaf coloration that is silver with dark olive veins.

The female parent differs from 'Flores Sea' in having leaves that are less silver in color, panicles that are less dense and in only blooming once per season. 'Flores Sea' can be most closely compared to *Heuchera* cultivars 'Cinnabar Silver' (U.S. Plant Pat. No. 18,324) and 'Silver Scrolls' (U.S. Plant Pat. No. 12,066). 'Cinnabar Silver' is similar to 'Flores Sea' in having foliage that is silver in color and flowers that are large in size. 'Cinnabar Silver' differs from 'Flores Sea' in having flowers that are more red in color, leaf petioles that are brown in color, and in having a shorter flowering period. 'Silver Scrolls' is similar to 'Flores Sea' in having foliage that is silver in color and in having a long blooming period. 'Silver Scrolls' differs from 'Flores Sea' in having leaves that are slightly smaller in size and flowers that are smaller in size and white in color.

BRIEF DESCRIPTION OF THE DRAWINGS

The accompanying colored photographs illustrate the overall appearance and distinct characteristics of the new *Heuchera*. The photographs were taken of a plant two years in age as grown outdoors in a 7.5 liter container in Pellenberg, The Netherlands.

The photograph in FIG. 1 provides a side view of the plant habit and foliage coloration of 'Flores Sea'.

Figure 1:
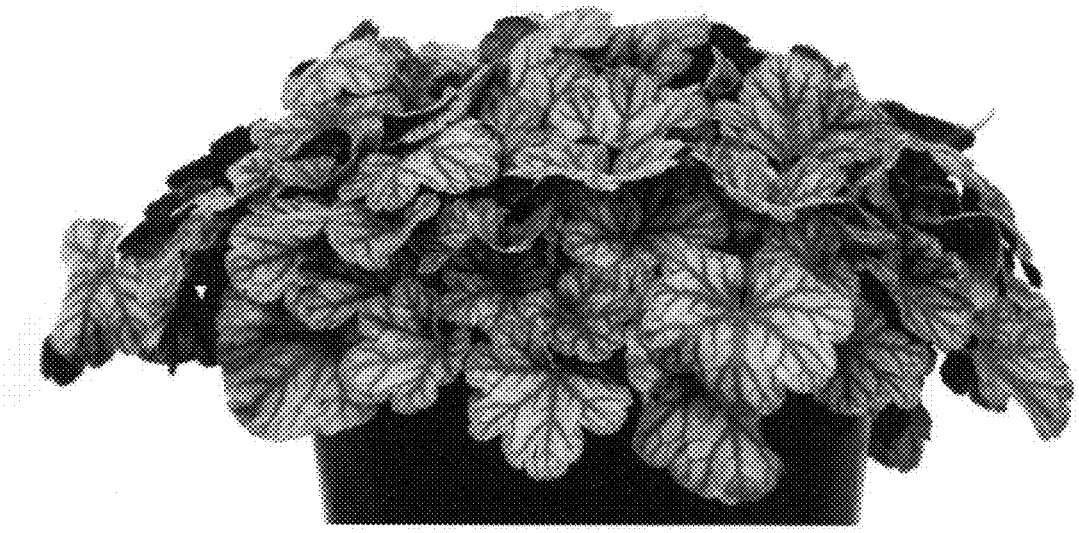
Figure 2:
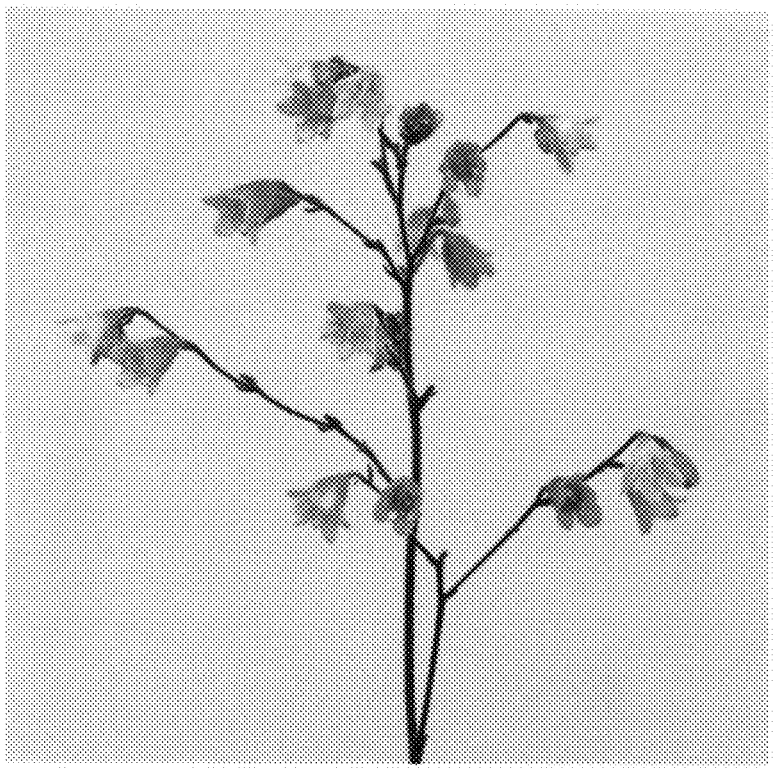

The photograph in FIG. 2 provides a close-up view of an inflorescence of 'Flores Sea'.

Figure 3:
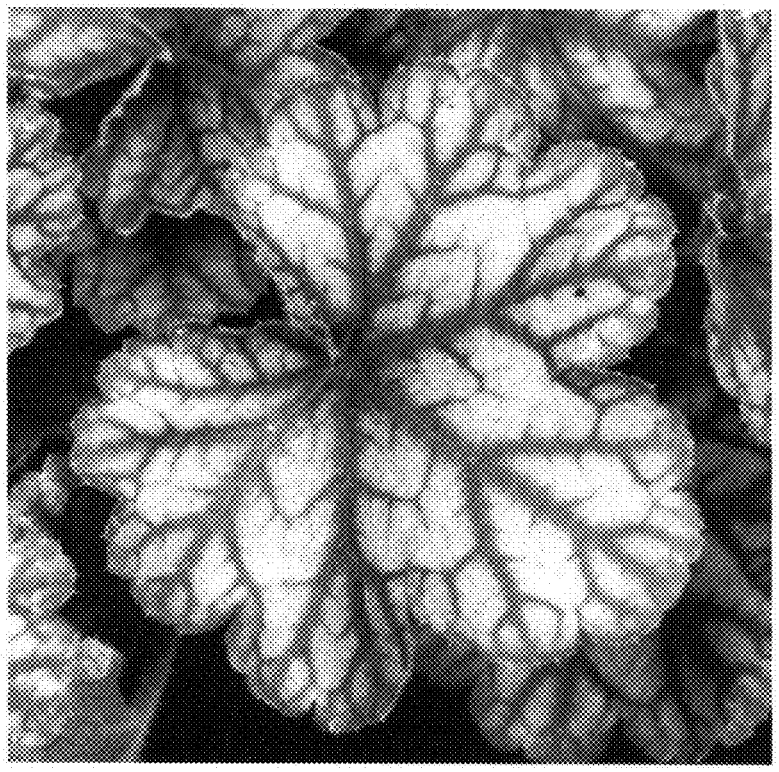

The photograph in FIG. 3 provides a close-up view of a leaf of 'Flores Sea'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year-old plants of the new cultivar as grown in an unheated greenhouse in 7.5-liter containers in Pellenberg, Belgium. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late spring and reblooming in summer in Belgium.

*Plant type.*—Herbaceous perennial.

*Plant habit.*—Clump-forming, flattened globular, mounded foliage.

*Height and spread.*—Average of 15.4 cm in height to top of foliage and 40 cm in height to top of inflorescences and an average of 50 cm in width.

*Hardiness.*—At least in U.S.D.A. Zone 3 to 9.

*Diseases and pests.*—Not more susceptible to pests and diseases than other *Heuchera* varieties.

*Root description.*—Fibrous roots on woody rootstalks, 162C in color.

*Branching habit.*—Basal rosette, no lateral branches.

*Basal branching.*—No lateral stems only basal rosettes.

*Propagation.*—Tissue culture.

*Root development.*—An average of 13 weeks to fully develop from a tissue culture plug in a 7-cm or larger container.

*Growth rate.*—Moderate to low vigor.

Foliage description:

*Leaf shape.*—Orbicular to broad ovate.

*Leaf division.*—Simple.

*Leaf base.*—Hastate, lobes slightly to moderately overlapping.

*Leaf apex.*—Obtuse.

*Leaf venation.*—Laciniate, upper surface color; N189A along primary and secondary veins with primary veins 148A towards the base, lower surface color; 177B.

*Leaf margins.*—Lobed with an average of 7 lobes per leaf, lobe margins crenate.

*Leaf attachment.*—Petiolate.

*Leaf arrangement.*—Alternate, basal rosettes.

*Leaf orientation.*—Typically nearly horizontal to slightly cupped under.

*Leaf surface.*—Upper surface slightly glossy, lower surface glossy, both surfaces densely pubescent, average of 0.75 mm in length and 155D in color.

*Leaf color.*—Young upper surface; closest to a range of 201A to 201B and N200B, but darker, young lower surface; range of N77B and N186D, mature and fall upper surface; 198A to 198B, mature and fall lower surface; range of N77B and N186D.

*Leaf size.*—Average of 6.5 cm in length and 6.9 cm in width.

*Leaf quantity.*—19 per basal rosette.

*Petioles.*—Round in shape, average of 8.8 cm in length and 2 mm in width, color; 148C, surface is densely pubescent with very short strigose hairs; an average of 1 mm in length and 155D in color.

*Stipules.*—Small leafy stipules at the base of each leaf, narrow acute apex, with an average of 1.5 cm in length and 5 mm in width, 70C to 70D in color, surface is moderately covered with short soft hairs.

Flower description:

*Inflorescence type.*—Axillary compound spike.

*Inflorescence size.*—An average of 10.3 cm in height from the lowest flower to the top and 8.7 cm in width.

*Inflorescence number.*—An average of 10 per 7.5-liter container.

*Flower fragrance.*—None.

*Flower quantity.*—Average of 40 flowers per inflorescence.

*Flower lastingness.*—Average of one week, self cleaning.

*Flower buds.*—Obovate in shape, an average of 3 mm in diameter and 5 mm in length, 58B to 58C in color.

*Flower aspect.*—Outward.

*Flower type.*—Single, campanulate.

*Flower size.*—Average of 9 mm in diameter and depth.

*Petals.*—Average of 5, rotate arrangement and implanted in the hypanthium at base, narrow rhomboidal to narrow obovate in shape, margin is entire, apex is acute, upper and lower surface is matte and smooth, color when opening and fully upper and lower surface 62B, 3 mm in length and 1 mm in width.

*Calyx.*—Campanulate, sepals fused to hypanthium, 9 mm in length and diameter.

*Sepals.*—5, fused into hypanthium, elliptic in shape, 9 mm in length and 3.5 mm in width, margin is entire fused into hypanthium, apex is broadly acute to obtuse, fused base, upper surface is matte, lower surface is moderately covered with very short glandular hairs an average of 0.3 mm in length and 62A in color, color; immature upper surface 62A, base 62D, immature lower surface; 62A, base 64D, mature upper surface 67C, mature lower surface 67C, base 64B.

*Peduncles.*—Moderate in strength, 2 mm in diameter, 28.4 cm in length, average angle of 85° to soil level, color ranging between 183A to 183B, densely covered with soft pubescence, 0.5 mm in length and 155D in color.

*Pedicels.*—Moderate in strength, average of 3 mm in length and 0.5 mm in diameter, held at an average angle of 40° (0° horizontal), 64D in color.

Reproductive organs:

*Gynoecium.*—Pistil; 2, stigma; pointed in shape, 4 mm in length, 150D in color, style; 2 mm in length, 150D in color, ovaries; superior and 150D in color.

*Androecium.*—Stamens; 5, anthers; ovate in shape, 0.2 mm in length and 155A in color, filament; 3 mm in length and 61C in color, pollen is low in quantity and 156A in color.

*Seed/fruit.*—No fruit or seeds detected to date.

It is claimed:

1. A new and distinct cultivar of *Heuchera* plant named 'Flores Sea' as herein illustrated and described.

* * * * *